(12) United States Patent
Patwardhan et al.

(10) Patent No.: US 8,777,854 B2
(45) Date of Patent: Jul. 15, 2014

(54) METHOD AND SYSTEM FOR ULTRASOUND BASED AUTOMATED DETECTION, QUANTIFICATION AND TRACKING OF PATHOLOGIES

(75) Inventors: Kedar Anil Patwardhan, Latham, NY (US); David Martin Mills, Niskayuna, NY (US)

(73) Assignee: General Electric Company, Niskayuna, NY (US)

( * ) Notice: Subject to any disclaimer, the term of this patent is extended or adjusted under 35 U.S.C. 154(b) by 370 days.

(21) Appl. No.: 13/249,270

(22) Filed: Sep. 30, 2011

(65) Prior Publication Data

US 2013/0060121 A1    Mar. 7, 2013

Related U.S. Application Data

(60) Provisional application No. 61/531,165, filed on Sep. 6, 2011.

(51) Int. Cl.
*A61B 8/00* (2006.01)

(52) U.S. Cl.
USPC ........... 600/437; 600/407; 600/410; 600/425; 600/476

(58) Field of Classification Search
USPC .................. 600/407, 410, 425, 437, 473, 476
See application file for complete search history.

(56) References Cited

U.S. PATENT DOCUMENTS

| | | | |
|---|---|---|---|
| 5,458,130 A | 10/1995 | Kaufman et al. | |
| 6,246,745 B1 * | 6/2001 | Bi et al. | 378/54 |
| 6,569,098 B2 | 5/2003 | Kawchuk | |
| 7,555,153 B2 | 6/2009 | Martel-Pelletier et al. | |
| 2004/0234116 A1 * | 11/2004 | Bi et al. | 382/132 |
| 2010/0106018 A1 | 4/2010 | Jiang et al. | |
| 2011/0021914 A1 | 1/2011 | Zheng et al. | |
| 2011/0112808 A1 | 5/2011 | Anderson et al. | |

OTHER PUBLICATIONS

Vincent et al., "Automatic delineation of the osseous interface in ultrasound images by information fusion" 2004, Proceedings of the International Conference on Information Fusion; 2; pp. 862-867 (not numbered).*

Tzu-Lun Weng, "Motion Segmentation and Estimation of Active Skeletal Muscles in Ultrasonic Image Sequences", Proceedings of the First Joint BMES/EMBS Conference 1999, vol. 2, pp. 1064, Oct. 1999.

Porter et al., "Three-Dimensional Registration and Fusion of Ultrasound and MRI Using Major Vessels as Fiducial Markers", IEEE Transactions on Medical Imaging, vol. 20, Issue 4, pp. 354-359, Apr. 2001.

Huang et al., "Development of a Portable 3D Ultrasound Imaging System for Musculoskeletal Tissues", Ultrasonics, vol. 43, Issue 3, pp. 153-163, Jan. 2005.

Loizides et al., "Optimizing Ultrasound-Guided Biopsy of Musculoskeletal Masses by Application of an Ultrasound Contrast Agent", Ultraschall Med, vol. 32, Issue 3, pp. 307-310, Jun. 2011.

* cited by examiner

*Primary Examiner* — James Kish
(74) *Attorney, Agent, or Firm* — Seema S. Katragadda

(57) ABSTRACT

An automated method for detecting a disease state is presented. The method includes identifying a bone surface in one or more image data sets, wherein the one or more data sets correspond to a region of interest in an object of interest. Furthermore, the method includes segmenting a joint capsule region corresponding to the one or more image data sets based on a corresponding identified bone surface. In addition, the method includes analyzing the segmented joint capsule region to identify the disease state. Systems and non-transitory computer readable medium configured to perform the automated method for detecting a disease state are also presented.

19 Claims, 9 Drawing Sheets

US 8,777,854 B2

METHOD AND SYSTEM FOR ULTRASOUND BASED AUTOMATED DETECTION, QUANTIFICATION AND TRACKING OF PATHOLOGIES

CROSS REFERENCE TO RELATED APPLICATIONS

This non-provisional application claims the benefit of priority under 35 U.S.C. §119(e) to U.S. Provisional Patent Application Ser. No. 61/531,165, filed Sep. 6, 2011, which is herein incorporated in its entirety by reference.

BACKGROUND

Embodiments of the present disclosure relate to ultrasound imaging, and more particularly to systems and methods for automated ultrasound based detection, quantification, and tracking of musculoskeletal pathologies over time.

Arthritis is a common cause of disability especially in the older population and it is one of the most chronic diseases in the U.S. Generally, the current musculoskeletal practice relies heavily on highly trained radiologists to perform and analyze images of the anatomy of interest. Unfortunately, this practice leads to additional time and cost in providing care to the patient.

Currently, imaging techniques like computed tomography (CT), magnetic resonance (MR) imaging, X-ray and the like are used in the diagnosis of arthritis. However, modalities like X-ray entail use of 2D projections of the anatomy and fail to paint an accurate picture of the underlying 3D structure of the anatomy. Also, other imaging methods like CT and MR are relatively expensive and are contraindicated for certain groups of patients (for example, patients with pacemakers cannot undergo MR scans).

Ultrasound imaging provides a relatively inexpensive method of imaging. Recent developments in ultrasound imaging have led to current state of the art ultrasound devices that boast of relatively high image resolutions and ease of use. These developments have led to increased use of ultrasound for clinical research as well as day to day point of care practice. Consequently, the number of rheumatologists using ultrasound has been steadily increasing over the years. Moreover, the improved ultrasound technology has led to higher frequency ultrasound probes that are well-suited for imaging relatively shallow anatomical structures, as is generally the case for musculoskeletal imaging.

Notwithstanding the various advantages of ultrasound, an important factor that restricts the use of ultrasound at the point of care has been the fact that performing ultrasound scanning requires experience and training of the clinician. In addition, use of 2D ultrasound leads to subjective diagnosis even among relatively skilled ultrasound practitioners. Moreover, three-dimensional (3D) (volumetric) ultrasound may be employed in the detection of musculoskeletal pathologies like bone erosions. 3D imaging also allows quantification of the progression of a particular musculoskeletal pathology, which would be very valuable in determining disease stage and corresponding treatment.

It is therefore desirable to design and develop dedicated methods and systems that provide faster and more accurate diagnosis of pathologies and assessment of treatment response for pathologies like musculoskeletal pathologies. Particularly, it is desirable to develop systems and methods that allow detection, quantification and/or tracking of the pathologies with greater ease of use, shorter learning period, faster exam time, and reduce operator dependence.

BRIEF DESCRIPTION

In accordance with aspects of the present technique, an automated method for detecting a disease state is presented. The method includes identifying a bone surface in one or more image data sets, wherein the one or more data sets correspond to a region of interest in an object of interest. Furthermore, the method includes segmenting a joint capsule region corresponding to the one or more image data sets based on a corresponding identified bone surface. In addition, the method includes analyzing the segmented joint capsule region to identify the disease state. A non-transitory computer readable medium including one or more tangible media, where the one or more tangible media include code adapted to perform the automated method for detecting a disease state is also presented.

In accordance with aspects of the present technique, an automated system for detecting a disease state is presented. The system includes a detection platform, where the detection platform includes a bone surface identifying module configured to identify a bone surface in one or more image data sets, wherein the one or more image data sets correspond to a region of interest in an object of interest, a joint capsule segmenting module configured to determine a joint capsule region in the one or more image data sets based on a corresponding identified bone surface, and an analysis module configured to identify the disease state in the segmented joint capsule region.

In accordance with yet another aspect of the present technique, an imaging system is presented. The system includes an acquisition subsystem configured to obtain a plurality of image data sets corresponding to a region of interest in an object of interest. Moreover, the system includes a processing subsystem in operative association with the acquisition subsystem and including a detection platform, wherein the detection platform includes a bone surface identifying module configured to identify a bone surface in one or more image data sets, wherein the one or more image data sets correspond to a region of interest in an object of interest, a joint capsule segmenting module configured to determine a joint capsule region in the one or more image data sets based on a corresponding identified bone surface, and an analysis module configured to identify a disease state in the segmented joint capsule region.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

As will be described in detail hereinafter, various methods and systems for the automated ultrasound based detection, quantification and tracking of pathologies are presented. Employing the method and system described hereinafter facilitates early diagnosis, quantification (scoring) and enhances longitudinal tracking of the pathologies, while reducing operator dependence in the assessment of pathologies. Moreover, a method for the objective assessment of the pathologies is presented, thereby enhancing the efficiency of the diagnosis of the pathologies.

Figure 1:
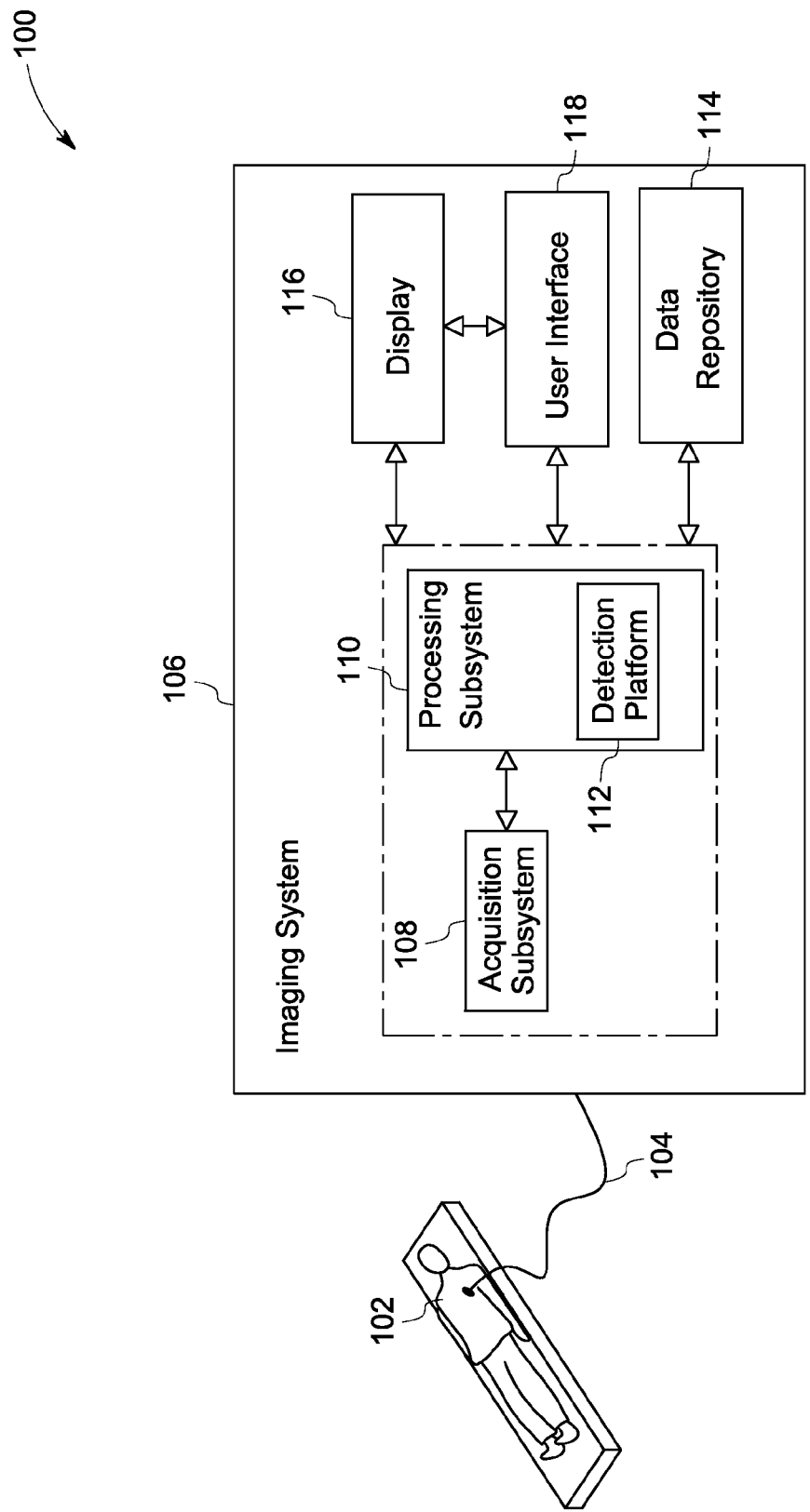
FIG. 1 is a diagrammatical illustration of a system for automated detection, quantification and tracking of pathologies in ultrasound images, in accordance with aspects of the present technique.

FIG. 1 is a block diagram of an exemplary system 100 for use in diagnostic imaging in accordance with aspects of the present technique. The system 100 is configured to facilitate automated detection, quantification and tracking of pathologies, such as musculoskeletal pathologies using ultrasound images corresponding to an anatomical region of interest in an object of interest. To that end, the system 100 may be configured to acquire image data from a patient 102. In one embodiment, the system 100 may acquire image data from the patient 102 via an image acquisition device 104. Also, in one embodiment, the image acquisition device 104 may include a probe, where the probe may include an invasive probe, or a non-invasive or external probe, such as an external ultrasound probe, that is configured to aid in the acquisition of image data. Also, in certain other embodiments, image data may be acquired via one or more sensors (not shown) that may be disposed on the patient 102. By way of example, the sensors may include physiological sensors (not shown) such as electrocardiogram (ECG) sensors and/or positional sensors such as electromagnetic field sensors or inertial sensors. These sensors may be operationally coupled to a data acquisition device, such as an imaging system, via leads (not shown), for example.

The system 100 may also include a medical imaging system 106 that is in operative association with the image acquisition device 104. It should be noted that although the exemplary embodiments illustrated hereinafter are described in the context of a medical imaging system, other imaging systems and applications such as industrial imaging systems and non-destructive evaluation and inspection systems, such as pipeline inspection systems, liquid reactor inspection systems, are also contemplated. Additionally, the exemplary embodiments illustrated and described hereinafter may find application in multi-modality imaging systems that employ ultrasound imaging in conjunction with other imaging modalities, position-tracking systems or other sensor systems. Furthermore, it should be noted that although the exemplary embodiments illustrated hereinafter are described in the context of a medical imaging system, such as an ultrasound imaging system, use of other imaging systems, such as, but not limited to, a magnetic resonance (MR) imaging system, an X-ray imaging system, a computed tomography (CT) imaging system, and other imaging systems is also contemplated in accordance with aspects of the present technique.

As noted hereinabove, in a presently contemplated configuration, the medical imaging system 106 may include an ultrasound imaging system. The medical imaging system 106 may include an acquisition subsystem 108 and a processing subsystem 110, in one embodiment. Further, the acquisition subsystem 108 of the medical imaging system 106 is configured to acquire image data representative of one or more anatomical regions of interest in the patient 102 via the image acquisition device 104, in one embodiment. Moreover, in one embodiment, the acquisition subsystem 108 may be configured to acquire one or more two-dimensional (2D) images of the anatomical region of interest. These 2D images may be employed to form a three-dimensional image volume. Alternatively, the acquisition subsystem 108 may be capable of acquiring a 3D image volume representative of the anatomical region of interest in the patient 102. Furthermore, the anatomical region of interest may include the bone joints in the patient 102. Accordingly, the acquisition subsystem 108 is configured to acquire a plurality of 2D, 3D and/or four-dimensional (4D) images representative of the bone joints in the patient 102, for example. It may be noted that the acquired images may be representative of images acquired at different points in time. Additionally, the image data acquired from the patient 102 may then be processed by the processing subsystem 110.

The image data acquired and/or processed by the medical imaging system 106 may be employed to aid a clinician in identifying disease states, assessing need for treatment, determining suitable treatment options, tracking the progression of the disease, and/or monitoring the effect of treatment on the disease states. It may be noted that the terms treatment and therapy may be used interchangeably. In certain embodiments, the processing subsystem 110 may be further coupled to a storage system, such as a data repository 114, where the data repository 114 is configured to store the acquired image data.

In accordance with exemplary aspects of the present technique, the processing subsystem 110 may include a detection platform 112 that is configured to aid in the detection, quantification and/or tracking of pathologies in the anatomical region of the patient 102. More particularly, the detection platform 112 may be configured to facilitate the detection of pathologies in the anatomical region of interest employing the images acquired via the medical imaging system 106 and will be described in greater detail with reference to FIGS. 3-9. As previously noted, the anatomical region of interest may be the bone joints in the patient 102. Additionally, in one embodiment, the detection platform 112 is configured to aid in the automated detection, quantification, and/or tracking of pathologies, such as musculoskeletal pathologies, using the acquired ultrasound images. Also, in one embodiment, the pathologies in the anatomical region of interest may include diseases such as rheumatoid arthritis in the patient 102. Although the present technique is described in terms of rheumatoid arthritis, it may be noted that use of the present technique for the detection of other bone related ailments is also envisaged.

Further, as illustrated in FIG. 1, the medical imaging system 106 may include a display 116 and a user interface 118. In certain embodiments, such as in a touch screen, the display 116 and the user interface 118 may overlap. Also, in some embodiments, the display 116 and the user interface 118 may include a common area. In accordance with aspects of the present technique, the display 116 of the medical imaging system 106 may be configured to display an image generated by the medical imaging system 106 based on the acquired image data. Additionally, in accordance with further aspects of the present technique, the pathologies detected by the detection platform 110 may be visualized on the display 116.

In addition, the user interface 118 of the medical imaging system 106 may include a human interface device (not shown) configured to aid the clinician in manipulating image data displayed on the display 116. The human interface device may include a mouse-type device, a trackball, a joystick, a stylus, or a touch screen configured to facilitate the clinician to identify the one or more regions of interest requiring therapy. However, as will be appreciated, other human interface devices, such as, but not limited to, a touch screen, may also be employed. Furthermore, in accordance with aspects of the present technique, the user interface 118 may be configured to aid the clinician in navigating through the images acquired by the medical imaging system 106. Additionally, the user interface 118 may also be configured to aid in manipulating and/or organizing the detected pathologies displayed on the display 116.

Figure 2:
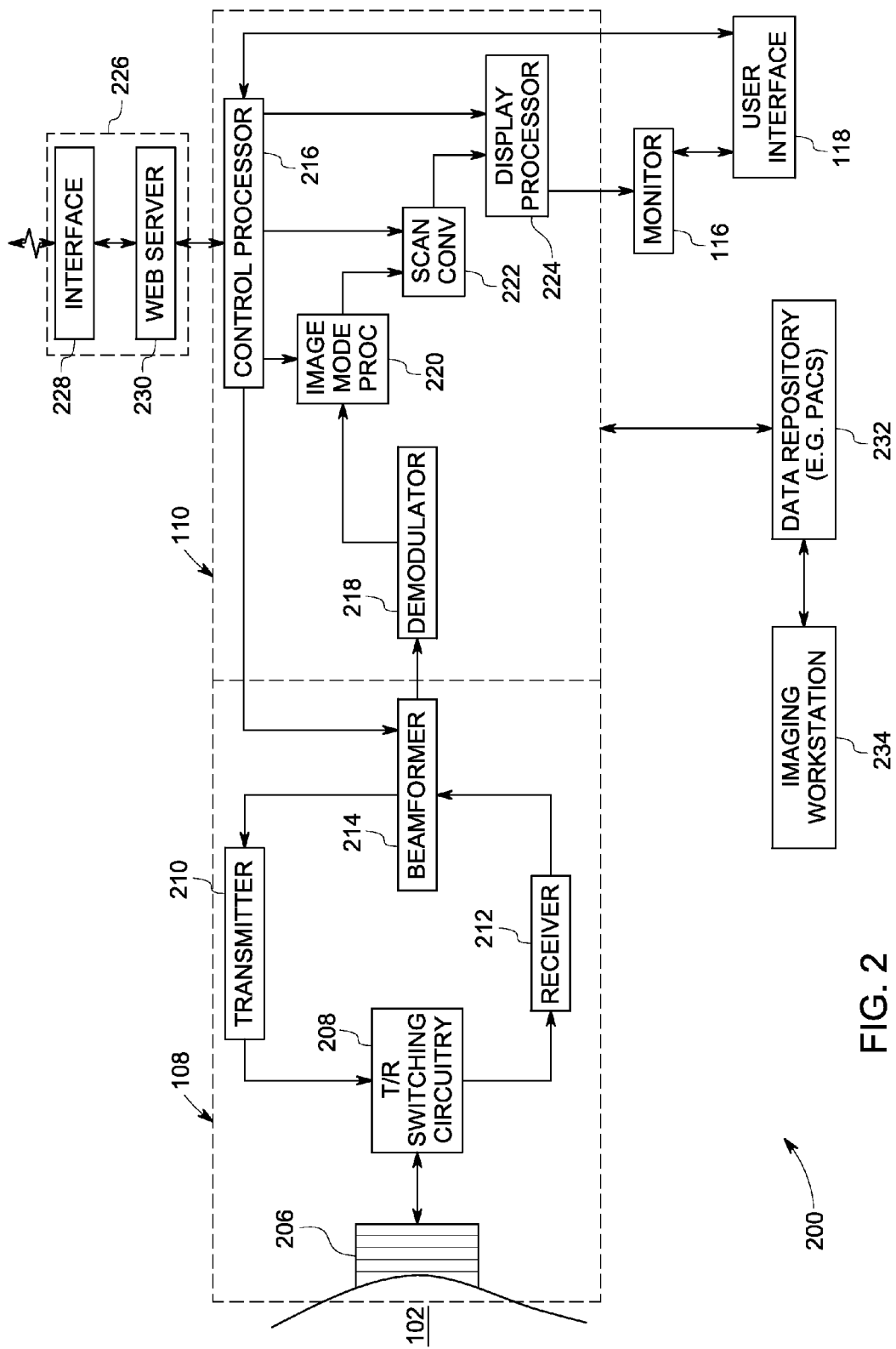
FIG. 2 is a diagrammatical illustration of an ultrasound imaging system for use in the system of FIG. 1.

As previously noted with reference to FIG. 1, the medical imaging system 106 may include an ultrasound imaging system. FIG. 2 is a block diagram of an embodiment of an ultrasound imaging system 200 depicted in FIG. 1. The ultrasound system 200 includes an acquisition subsystem, such as the acquisition subsystem 108 of FIG. 1 and a processing subsystem, such as the processing subsystem 110 of FIG. 1. The acquisition subsystem 108 may include a transducer assembly 206. In addition, the acquisition subsystem 108 includes transmit/receive switching circuitry 208, a transmitter 210, a receiver 212, and a beamformer 214. It may be noted that in certain embodiments, the transducer assembly 206 is disposed in the probe 104 (see FIG. 1). Also, in certain embodiments, the transducer assembly 206 may include a plurality of transducer elements (not shown) arranged in a spaced relationship to form a transducer array, such as a one-dimensional or two-dimensional transducer array, for example. Additionally, the transducer assembly 206 may include an interconnect structure (not shown) configured to facilitate operatively coupling the transducer array to an external device (not shown), such as, but not limited to, a cable assembly or associated electronics. In the illustrated embodiment, the interconnect structure may be configured to couple the transducer array to the T/R switching circuitry 208.

The processing subsystem 110 includes a control processor 216, a demodulator 218, an imaging mode processor 220, a scan converter 222 and a display processor 224. The display processor 224 is further coupled to a display monitor, such as the display 116 (see FIG. 1), for displaying images. User interface, such as the user interface area 118 (see FIG. 1), interacts with the control processor 216 and the display monitor 116. The control processor 216 may also be coupled to a remote connectivity subsystem 226 including a remote connectivity interface 228 and a web server 230. The processing subsystem 110 may be further coupled to a data repository 232, such as the data repository 114 of FIG. 1, configured to receive and/or store ultrasound image data. The data repository 232 interacts with an imaging workstation 234.

The aforementioned components may be dedicated hardware elements such as circuit boards with digital signal processors or may be software running on a general-purpose computer or processor such as a commercial, off-the-shelf personal computer (PC). The various components may be combined or separated according to various embodiments of the invention. Thus, those skilled in the art will appreciate that the present ultrasound imaging system 200 is provided by way of example, and the present techniques are in no way limited by the specific system configuration.

In the acquisition subsystem 108, the transducer assembly 206 is in contact with the patient 102 (see 206 FIG. 1). The transducer assembly 206 is coupled to the transmit/receive (T/R) switching circuitry 208. Also, the T/R switching circuitry 208 is in operative association with an output of transmitter 210 and an input of the receiver 212. The output of the receiver 212 is an input to the beamformer 214. In addition, the beamformer 214 is further coupled to the input of the transmitter 210 and to the input of the demodulator 218. The beamformer 214 is also operatively coupled to the control processor 216 as shown in FIG. 2.

In the processing subsystem 110, the output of demodulator 218 is in operative association with an input of the imaging mode processor 220. Additionally, the control processor 216 interfaces with the imaging mode processor 220, the scan converter 222 and the display processor 224. An output of imaging mode processor 220 is coupled to an input of scan converter 222. Also, an output of the scan converter 222 is operatively coupled to an input of the display processor 224. The output of display processor 224 is coupled to the monitor 116.

The ultrasound system 200 transmits ultrasound energy into the patient 102 and receives and processes backscattered ultrasound signals from the patient 102 to create and display an image. To generate a transmitted beam of ultrasound energy, the control processor 216 sends command data to the beamformer 214 to generate transmit parameters to create a beam of a desired shape originating from a certain point at the surface of the transducer assembly 206 at a desired steering angle. The transmit parameters are sent from the beamformer 214 to the transmitter 210. The transmitter 210 uses the transmit parameters to properly encode transmit signals to be sent to the transducer assembly 206 through the T/R switching circuitry 208. The transmit signals are set at certain levels and phases with respect to each other and are provided to individual transducer elements of the transducer assembly 206. The transmit signals excite the transducer elements to emit ultrasound waves with the same phase and level relationships. As a result, a transmitted beam of ultrasound energy is formed in the patient 102 along a scan line when the transducer assembly 206 is acoustically coupled to the patient 102 by using, for example, ultrasound gel. The process is known as electronic scanning.

In one embodiment, the transducer assembly 206 may be a two-way transducer. When ultrasound waves are transmitted into a patient 102, the ultrasound waves are backscattered off the tissue and blood samples within the patient 102. The transducer assembly 206 receives the backscattered waves at different times, depending on the distance into the tissue they return from and the angle with respect to the surface of the transducer assembly 206 at which they return. The transducer elements convert the ultrasound energy from the backscattered waves into electrical signals.

The electrical signals are then routed through the T/R switching circuitry 208 to the receiver 212. The receiver 212 amplifies and digitizes the received signals and provides other functions such as gain compensation. The digitized received signals corresponding to the backscattered waves received by each transducer element at various times preserve the amplitude and phase information of the backscattered waves.

The digitized signals are sent to the beamformer 214. The control processor 216 sends command data to beamformer 214. The beamformer 214 uses the command data to form a receive beam originating from a point on the surface of the transducer assembly 206 at a steering angle typically corresponding to the point and steering angle of the previous ultrasound beam transmitted along a scan line. The beamformer 214 operates on the appropriate received signals by performing time delaying and focusing, according to the instructions of the command data from the control processor 216, to create received beam signals corresponding to sample volumes along a scan line within the patient 102. The phase, amplitude, and timing information of the received signals from the various transducer elements are used to create the received beam signals.

The received beam signals are sent to the processing subsystem 110. The demodulator 216 demodulates the received beam signals to create pairs of I and Q demodulated data values corresponding to sample volumes along the scan line. Demodulation is accomplished by comparing the phase and amplitude of the received beam signals to a reference frequency. The I and Q demodulated data values preserve the phase and amplitude information of the received signals.

The demodulated data is transferred to the imaging mode processor 220. The imaging mode processor 220 uses parameter estimation techniques to generate imaging parameter values from the demodulated data in scan sequence format. The imaging parameters may include parameters corresponding to various possible imaging modes such as B-mode, color velocity mode, spectral Doppler mode, and tissue velocity imaging mode, for example. The imaging parameter values are passed to the scan converter 222. The scan converter 222 processes the parameter data by performing a translation from scan sequence format to display format. The translation includes performing interpolation operations on the parameter data to create display pixel data in the display format.

The scan converted pixel data is sent to the display processor 224 to perform any final spatial or temporal filtering of the scan converted pixel data, to apply grayscale or color to the scan converted pixel data, and to convert the digital pixel data to analog data for display on the monitor 116. The user interface 118 is coupled to the control processor 216 to allow a user to interface with the ultrasound system 200 based on the data displayed on the monitor 116.

Figure 3:
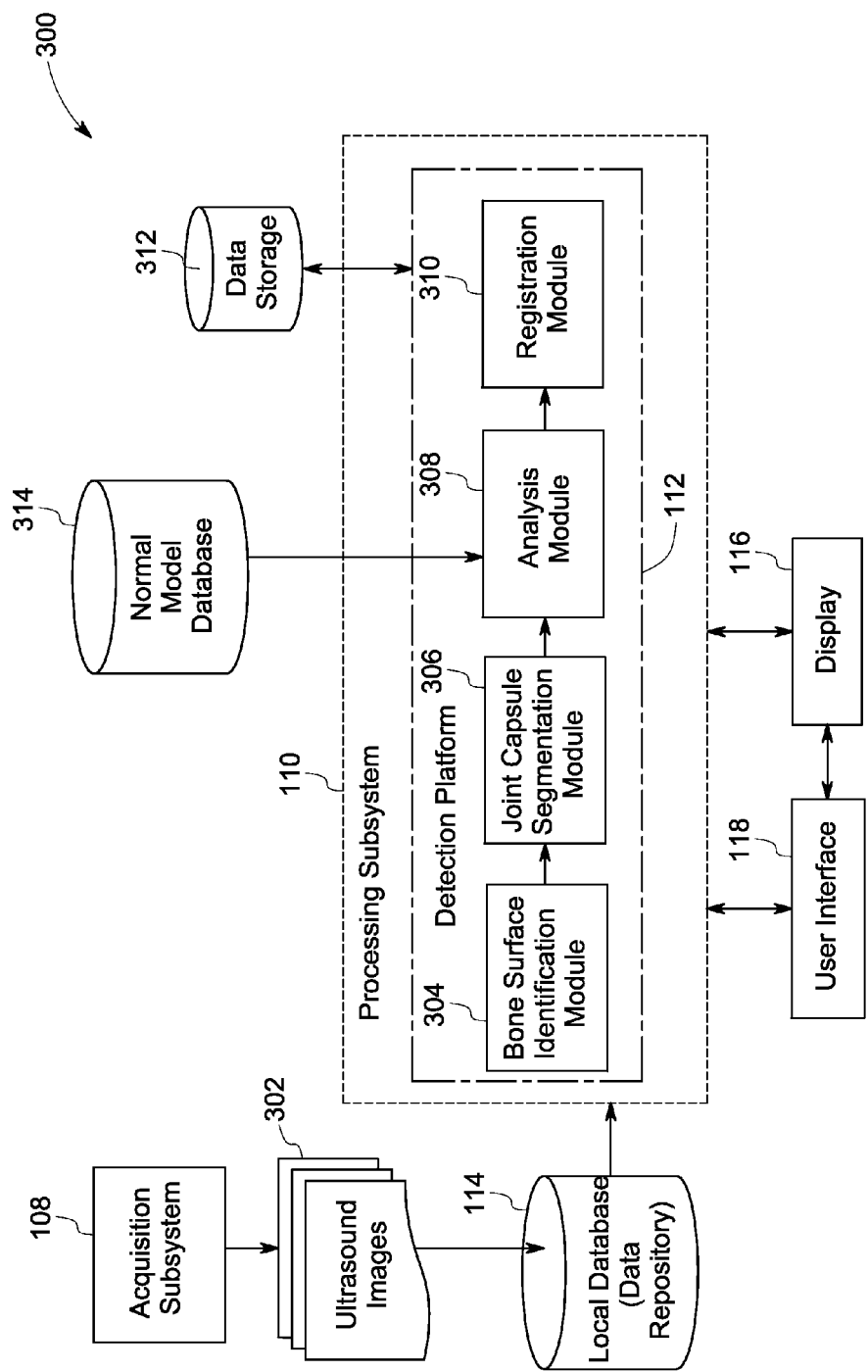
FIG. 3 is a diagrammatical illustration of one embodiment of the system of FIG. 1, in accordance with aspects of the present technique.

Turning now to FIG. 3, a block diagram 300 of one embodiment of the diagnostic system 100 of FIG. 1 is depicted. As previously noted with reference to FIG. 1, the acquisition subsystem 108 (see FIG. 1) is configured to aid in the acquisition of image data from the patient 102 (see FIG. 1). Accordingly, one or more images representative of the patient 102 may be acquired by the acquisition subsystem 108. In certain embodiments, the one or more images may include ultrasound images 302. It may be noted that the ultrasound images 302 may be representative of an anatomical region in the patient 102. For instance, in the example illustrated in FIG. 3, the ultrasound images 302 may include image data representative of a bone joint region of the patient 102. As previously noted, the ultrasound images 302 may include 2D images, 3D images and/or 4D images. Also, as previously noted, the 2D, 3D and/or 4D images 302 may include longitudinal images that are acquired at different points in time.

Furthermore, the image data acquired by the acquisition subsystem 108 may be stored in the data repository 114 (see FIG. 1). In certain embodiments, the data repository 114 may include a local database. The detection platform 112 (see FIG. 1) may then access these images, such as the ultrasound images 302, from the local database 114. Alternatively, the ultrasound images 302 may be obtained by the acquisition subsystem 108 from an archival site, a database, or an optical data storage article. For example, the acquisition subsystem 108 may be configured to acquire images stored in the optical data storage article. It may be noted that the optical data storage article may be an optical storage medium, such as a compact disc (CD), a digital versatile disc (DVD), multi-layer structures, such as DVD-5 or DVD-9, multi-sided structures, such as DVD-10 or DVD-18, a high definition digital versatile disc (HD-DVD), a Blu-ray disc, a near field optical storage disc, a holographic storage medium, or another like volumetric optical storage medium, such as, for example, two-photon or multi-photon absorption storage format. Further, these ultrasound images 302 so acquired by the acquisition subsystem 108 may be stored locally on the medical imaging system 106 (see FIG. 1). The ultrasound images 302 may be stored in the local database 114, for example.

Moreover, as previously noted with reference to FIG. 1, the processing subsystem 110 (see FIG. 1) is configured to process these ultrasound images 302, to aid the clinician in identifying disease states, assessing need for treatment, determining suitable treatment options, tracking the progression of the disease states, and/or monitoring the effect of treatment on the disease states. More particularly, the processing subsystem 110 may be configured to aid in the detection, quantification and/or tracking of pathologies in one or more anatomical regions in the patient 102. In one example, the processing subsystem 110 may be configured to aid in the detection, quantification and/or tracking of musculoskeletal pathologies using the ultrasound images 302 that are representative of the one or more anatomical regions in the patient 102, such as the bone joints of the patient 102. Also, in the embodiments illustrated in FIGS. 1-2, the processing subsystem 110 is shown as including the detection platform 112, where the detection platform 112 is configured to aid in the detection, quantification and/or tracking of the musculoskeletal pathologies by employing the acquired ultrasound images 302, as previously described. However, the detection platform 112 may also be used as a standalone module that is physically separate from the processing subsystem 110 and the medical imaging system 106. By way of example, the detection platform 112 may be operationally coupled to the medical imaging system 106 and configured to aid in detection, quantification and/or tracking the musculoskeletal pathologies associated with the anatomical region in the patient 102 using the acquired ultrasound images 302.

In accordance with aspects of the present technique, the detection platform 112 is configured to aid in the identification, quantification and/or tracking of a disease state, such as, but not limited to, a musculoskeletal pathology. To that end, in accordance with aspects of the present technique, the detection platform 112 is configured to aid in the detection, quantification and/or tracking of the disease state by identifying a bone surface in the plurality of image data sets 302, segmenting a joint capsule region in the plurality of image data sets 302 using a corresponding identified bone surface, analyzing the identified bone surface and/or the segmented joint capsule region to identify, quantify and/or track a disease state. In certain other embodiments, the detection platform 112 may also be employed to aid in the detection and/or tracking of the disease state by registering the plurality of image data sets 302 using the corresponding identified bone surfaces to generate a registered image.

Moreover, in one embodiment, the detection platform 112 may include a bone surface identification module 304, a joint capsule segmentation module 306, and an analysis module 308. The detection platform 112 may also include a registration module 310, in certain embodiments. It may be noted that although the configuration of FIG. 3 depicts the detection platform 112 as including the bone surface identification module 304, the joint capsule segmentation module 306, the analysis module 308 and the registration module 310, fewer or more number of such modules may be used.

With continuing reference to FIG. 3, in a presently contemplated configuration, the bone surface identification module 304 is configured to identify a bone surface of the bone joint using the plurality of image data sets. As used herein, the term the plurality of image data sets is used to refer to the ultrasound images 302 acquired by the acquisition subsystem 108. It may be noted that the terms a plurality of image data sets and ultrasound images are used interchangeably. Furthermore, it may also be noted that the term pathology and disease state are used interchangeably. Additionally, in certain embodiments, the plurality of images 302 may be obtained during one clinical visit. For example, the plurality of images 302 may be acquired on the same day, at different points in time. In one embodiment, the different points in time may be within a few minutes of one another or may be spread out over the day. Additionally, the plurality of images 302 may also be acquired at multiple clinical visits that may be spread over weeks, months or even years to facilitate tracking disease progression and/or potential response to therapy.

The bone surface identification module 304 is configured to automatically identify and extract an articular bone surface using the ultrasound images 302. It may be noted that the bone surface identification module 304 is configured to identify and extract the bone surface corresponding to each of the ultrasound images 302. The articular bone surface so identified may be employed to enhance the efficiency of visual detection of musculoskeletal pathologies, such as erosion of the joint surface. Moreover, the articular bone surface so identified may also be employed to enable the automated detection and quantification of bone related pathologies, such as the erosion of the bone surface. To that end, the bone surface identification module 304 may also be configured to aid in the visualization of the identified articular bone surface, in certain embodiments.

Moreover, the joint capsule segmenting module 306 in the detection platform 112 is configured to segment a joint capsule region in the ultrasound images 302 using a corresponding bone surface identified by the bone surface identification module 304. For example, the joint capsule segmenting module 306 is configured to automatically segment the joint capsule region in the bone joints that include the meta-carpophalangeal (MCP) joint and/or the meta-tarsophalangeal (MTP) joint using the corresponding identified bone surface.

Subsequently, the segmented joint capsule region may be analyzed to detect and/or quantify any pathology, such as inflammations and the like. In addition, the segmented joint capsule region may be analyzed to allow statistical analysis of echogenicity as well as Doppler color-flow measurements within the joint capsule region to aid in the detection, quantification and/or tracking of pathologies, such as bone erosions, for example. In one embodiment, the analysis module 308 in the detection platform 112 is configured to analyze the identified bone surface and/or the segmented joint capsule region to identify the musculoskeletal pathology, track the musculoskeletal pathology, and/or study the efficacy of treatment on the musculoskeletal pathology. By way of example, the analysis module 308 may process the ultrasound images 302 and the segmented joint capsule region in particular to track any changes in the articular anatomy and determine corresponding quantitative and/or qualitative measurements.

Additionally, the analysis module 308 is also configured to process the ultrasound images 302, the extracted articular bone surface and/or the segmented joint capsule region to determine an objective volumetric measure of inflammatory changes at the bone joint level. By way of example, the ultrasound images 302 may be processed to provide a direct and intuitive volumetric visualization of the inflamed tissues, volumetric quantification, and/or volumetric Doppler flow assessment. Moreover, the analysis module 308 may also be configured to generate a score or a metric corresponding to the disease state, where the score or metric provides a direct joint-level assessment of the disease state at a point of care, such as a rheumatologist's office. In one embodiment, the analysis module 308 may be configured to determine the score or metric, the disease state and the like by comparing the determined score or metric with measurements corresponding to normal subjects. The normal measurements may be stored in a normal model database 314, for example.

It may be noted that in certain embodiments, the analysis module 308 may also be configured to aid a clinician in determining the disease state. To that end, the analysis module 308 may be configured to aid in the visualization of images indicative of the identified disease state and/or the generated metric. These images and/or metric(s) may be presented to the clinician. The clinician may then utilize these images and/or metric(s) to diagnose or determine a disease state, track the progression of the disease state, and/or study the efficacy of the therapy on the disease state.

As previously noted, in certain embodiments, the detection platform 112 may also include the registration module 310. The registration module 310 may be employed to register the ultrasound images 302 based on the identified bone surfaces to generate a registered image. The registered image is used to track the pathology in the bone joint, for instance. Moreover, the registered image, the extracted bone surfaces, and/or the segmented joint capsule regions may be stored in a data storage 312, in certain embodiments. In addition, the extracted bone surfaces, the segmented joint capsule regions, and/or the registered image may be visualized for display on the display 116, for example. Furthermore, the clinician may annotate, organize and/or annotate the displayed images using the user interface 118, in one embodiment.

Figure 4:
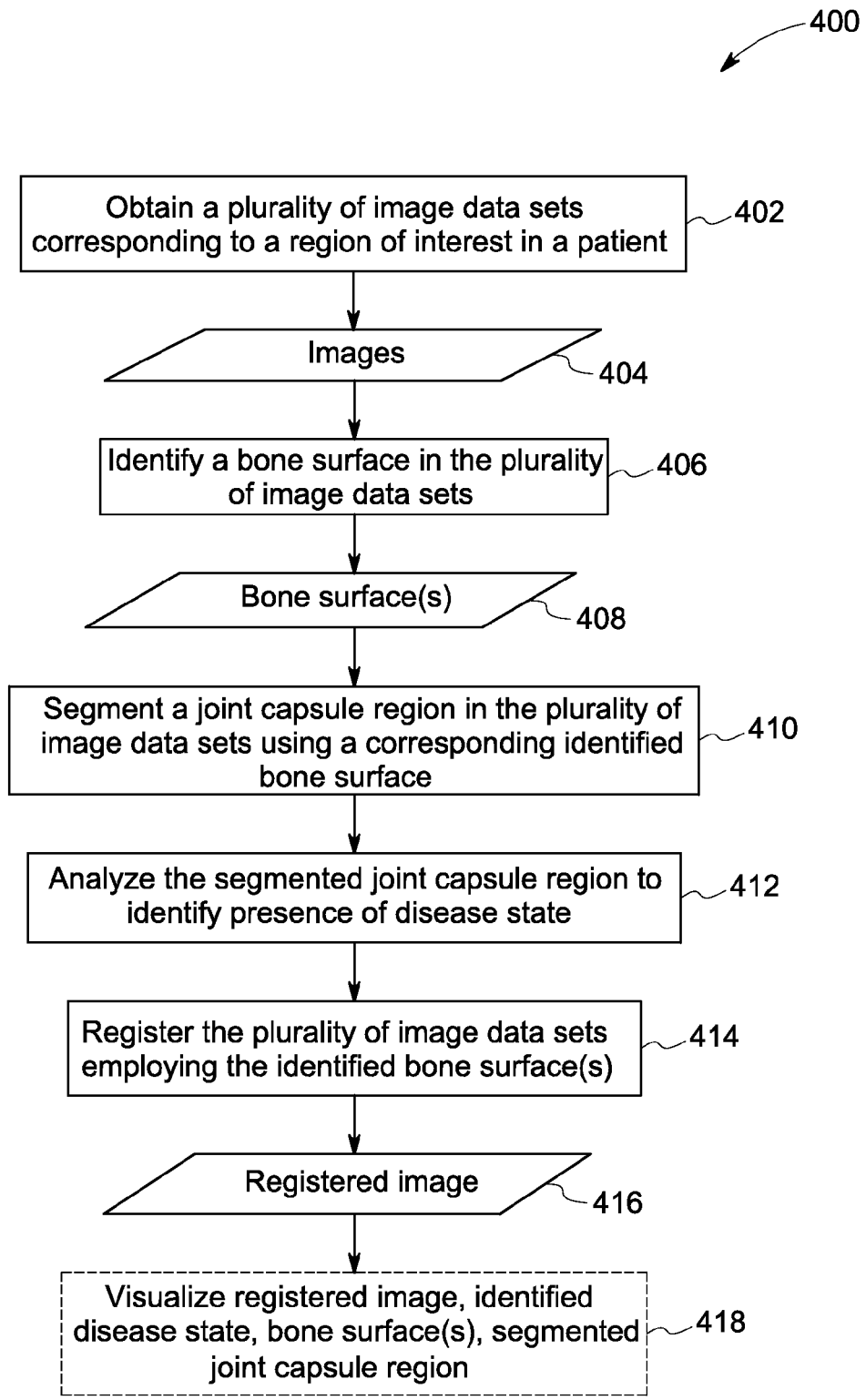
FIG. 4 is a flow chart depicting an exemplary method for automated detection, quantification and tracking of pathologies in ultrasound images, in accordance with aspects of the present technique.

The working of the detection platform 112, and the working of the bone surface identification module 304, the joint capsule segmentation module 306, the analysis module 308, and the registration module 310, in particular, may be better understood with reference to the exemplary logic depicted in FIG. 4. Turning now to FIG. 4, a flow chart of exemplary logic 400 for a method for tracking of pathologies such as musculoskeletal pathologies in an anatomical region of interest in the patient 102 (see FIG. 1) is illustrated. It may be noted that the method of FIG. 4 is described in terms of the various components of FIGS. 1-3.

Furthermore, the method 400 may be described in a general context of computer executable instructions. Generally, computer executable instructions may include routines, programs, objects, components, data structures, procedures, modules, functions, and the like that perform particular functions or implement particular abstract data types. Moreover, in certain embodiments, the computer executable instructions may be located in computer storage media, such as a memory, local to the imaging system 100 (see FIG. 1) and in operative association with the processing subsystem 110 (see FIG. 1). In certain other embodiments, the computer executable instructions may be located in computer storage media, such as memory storage devices, that are removed from the imaging system. Moreover, the method for automated detection of pathologies using the ultrasound images 302 (see FIG. 3) includes a sequence of operations that may be implemented in hardware, software, or combinations thereof.

In the example presented in FIG. 4, a method for automated detection, quantification and/or tracking of musculoskeletal pathologies in the bone joints using ultrasound image data is presented. Accordingly, as previously noted, ultrasound images, such as the ultrasound images 302 representative of the bone joint region in the patient 102 may be employed to aid in the diagnosis and/or treatment of musculoskeletal pathologies.

The method starts at step 402 where one or more image data sets 404 representative of an anatomical region is obtained. In the present example, the method for detection of pathologies is described in terms of detection of musculoskeletal pathologies in bone joints of a patient, such as the patient 102 (see FIG. 1). Accordingly, the image data sets 404 may include ultrasound image data representative of the bone joint region of the patient 102. It may be noted that the image data sets 404 may include 2D, 3D and/or 4D ultrasound images. As previously noted, the image data sets 404 may be acquired in real-time from the patient 102 at different points in time. However, the image data sets 404 may instead be obtained from a data repository, such as the data repository 114 (see FIG. 1).

Furthermore, the plurality of image data sets 404 may be representative of longitudinal images. As used herein, the term "longitudinal images" is used to refer to images corresponding to the anatomical region of interest in an object of interest, such as the patient 102 acquired at different points in time. Accordingly, at step 402 one or more longitudinal images 404 are acquired. In the present example the ultrasound images 404 may be representative of a bone joint region in the patient 102. By way of example, 2D, 3D and/or 4D ultrasound images representative of a joint region in the patient 102 may be acquired. These longitudinal images 404 may be used in the diagnosis, therapy and/or follow-up studies.

In accordance with aspects of the present technique, the method for automated detection of pathologies in the ultrasound images 404 entails identification of a bone surface, as indicated by step 406. As previously noted, the bone surface identification module 304 (see FIG. 3) is employed to aid in the identification of the bone surface.

It may be noted that the identification of the bone surface relies on characteristic acoustic properties of different tissues in the anatomical region of interest in order to differentiate the various tissues in the ultrasound image 404. Accordingly, the characteristic acoustic response of the bone surface is employed to identify the bone surface. In particular, since the bone is substantially opaque to acoustic waves, when an acoustic wave impinges on the surface of the bone, almost all of the acoustic wave is reflected away from the bone and may return to the ultrasound transducer 206 (see FIG. 2). This reflection of the acoustic wave results in an acoustic "shadow" under the bone surface as a relatively small portion of the impinging acoustic wave is able to propagate under the bone surface. For example, about 5-10% of the impinging acoustic wave may be able to propagate under the bone surface. The acoustic shadow so formed results in a characteristic ultrasound image representation of the bone surface.

According to further aspects of the present technique, this characteristic ultrasound image representation of the bone surface is employed to facilitate an automated identification of the bone surface. In certain embodiments, specific image processing filters that are tailored to generate a strong response at the surface of the bone may be designed and employed to enable the automated identification of bone surface from the ultrasound image 404. The response to such filters is then used to generate a "bone-likelihood" $L(x)$, where x is the location of an arbitrary pixel in the ultrasound image 404 and $L(x)$ is the likelihood that there is a bone-tissue interface at or near x.

Furthermore, at step 406, once the bone surface is identified, the bone surface is extracted or segmented based on the generated bone surface likelihood. Numerous fast segmentation methods may be used to extract the bone surface. In certain embodiments, a graph based segmentation method that is extended to three dimensions may be employed to identify the bone surface in 3D. Consequent to the processing of step 406, the bone surface 408 is identified and extracted.

In certain situations, the bone surface 408 may curve away from the direction of the acoustic beam generated by the ultrasound probe 104. Accordingly, the acoustic beam from the probe 104 impinges on the bone surface 408 at an angle, thereby directing the reflected energy away from the probe 104 and resulting in a bone "drop-off" effect. In particular, only a relatively small portion of the energy is reflected in the direction of the transducer 206 resulting in relatively lower intensity echoes from the bone surface 408. This drop-off effect disadvantageously leads to failure of the bone identification in areas of lower echo intensity from the bone surface 408.

In accordance with aspects of the present technique, the drop-off effect is circumvented via use of an implicit bone surface normal computation in order to estimate the angle that the normal to the bone surface subtends with the ultrasound beam. This angle may be used to generate an intensity corrected ultrasound image. The angle may also be used to directly modify a bone-likelihood estimate and bone surface fitting. In certain embodiments, the surface fitting may entail an optimization algorithm, such as dynamic programming, which identifies the bone surface that passes through the highest values of a bone-likelihood map and at the same time maintains reasonable physical properties of the bone surface, such as smoothness.

Additionally, in accordance with further aspects of the present technique, once the bone surface 408 is identified, a joint capsule region is segmented, as indicated by step 410. As previously noted, the joint capsule segmentation module 306 is employed to segment the joint capsule region based on the identified bone surface 408. The joint capsule region is automatically segmented from the ultrasound image 404 based on the extracted bone surface 408. In one embodiment, the extracted bone surface 408 is employed to provide contextual indications about the location of the joint capsule region. Moreover, since most human joints have a particular anatomical structure, the anatomical structure of the joint is used to generate an anatomical atlas of the joint. Accordingly, an atlas based segmentation of the joint capsule based on the identified bone surface 408 is performed. In certain embodiments, such a segmentation of the joint capsule regions may also be performed based on user input in terms of manually seeding (initiating) the segmentation and subsequently performing an image based segmentation.

Once the joint capsule region is segmented, the segmented joint capsule region is analyzed to identify presence of any disease state in the joint, as indicated by step 412. The disease state may include musculoskeletal pathologies such as bone erosion, for example. In accordance with further aspects of the present technique, the segmented joint capsule region is also analyzed to aid in the quantification of the identified disease state. By way of example, the disease state of the segmented joint capsule region may be quantified by providing a score or a metric that is indicative of the severity of the disease. The analysis module 308 is used to identify any disease state, as previously noted with reference to FIG. 3.

It may be noted that the automated steps of the bone surface identification, the joint capsule region segmentation and analysis of the joint capsule region to identify and/or quantify the disease state may be performed for every patient scan. In addition, the automated steps also aid in the tracking of the progression of the disease state and/or in the evaluation of the efficacy of the therapy on the disease state. Accordingly, the plurality of acquired ultrasound images 404 is used to track the progression of the pathology and/or study the efficacy of treatment on the pathology, for example.

In certain embodiments, the acquired ultrasound images 404 may be registered, as depicted by step 414. In particular, assuming that the surface of the bone remains relatively unchanged, the bones surfaces across the ultrasound images 404 acquired at different points in time are employed to aid in the registration of the ultrasound images. Consequent to the registration step 414, a registered image 416 may be generated. The registration module 310 is utilized to register the ultrasound images 404.

Also, visual overlays of any changes in the anatomy between the ultrasound images 404 may be displayed on the display 116 (see FIG. 1), as indicated by step 418. In addition, the identified disease state, the identified bone surface 408, the segmented joint capsule region, and/or the registered image 416 may also be displayed on the display 116. This visualization allows the clinicians or users to understand and interpret the changes occurring at a particular joint over time. Steps 402-418 may be better understood with reference to FIGS. 5-9.

Figure 5:
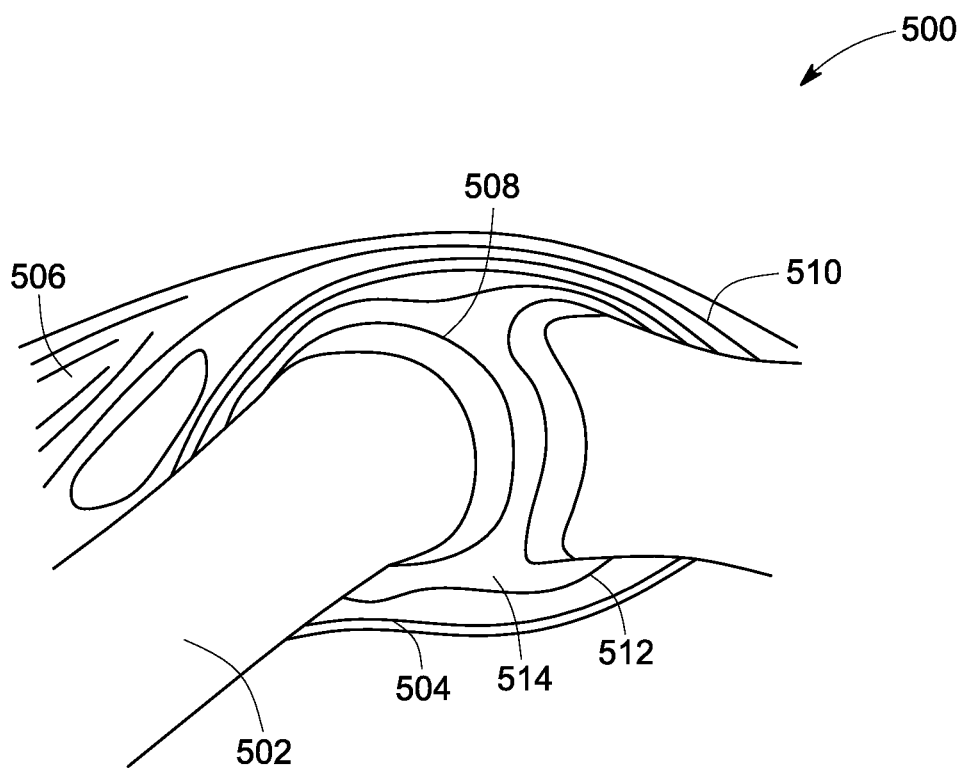
FIG. 5 is a diagrammatical illustration of a normal bone joint.

FIG. 5 is a diagrammatical illustration 500 of a normal human joint. Reference numeral 502 is representative of a bone in the joint 500, while a joint capsule is represented by reference numeral 504. Furthermore, reference numeral 506 is representative of a muscle, while a cartilage is represented by reference numeral 508. Moreover, a tendon is represented by reference numeral 510, while reference numeral 512 is representative of the synovium. Also, synovial fluid is represented by reference numeral 514.

Figure 6:
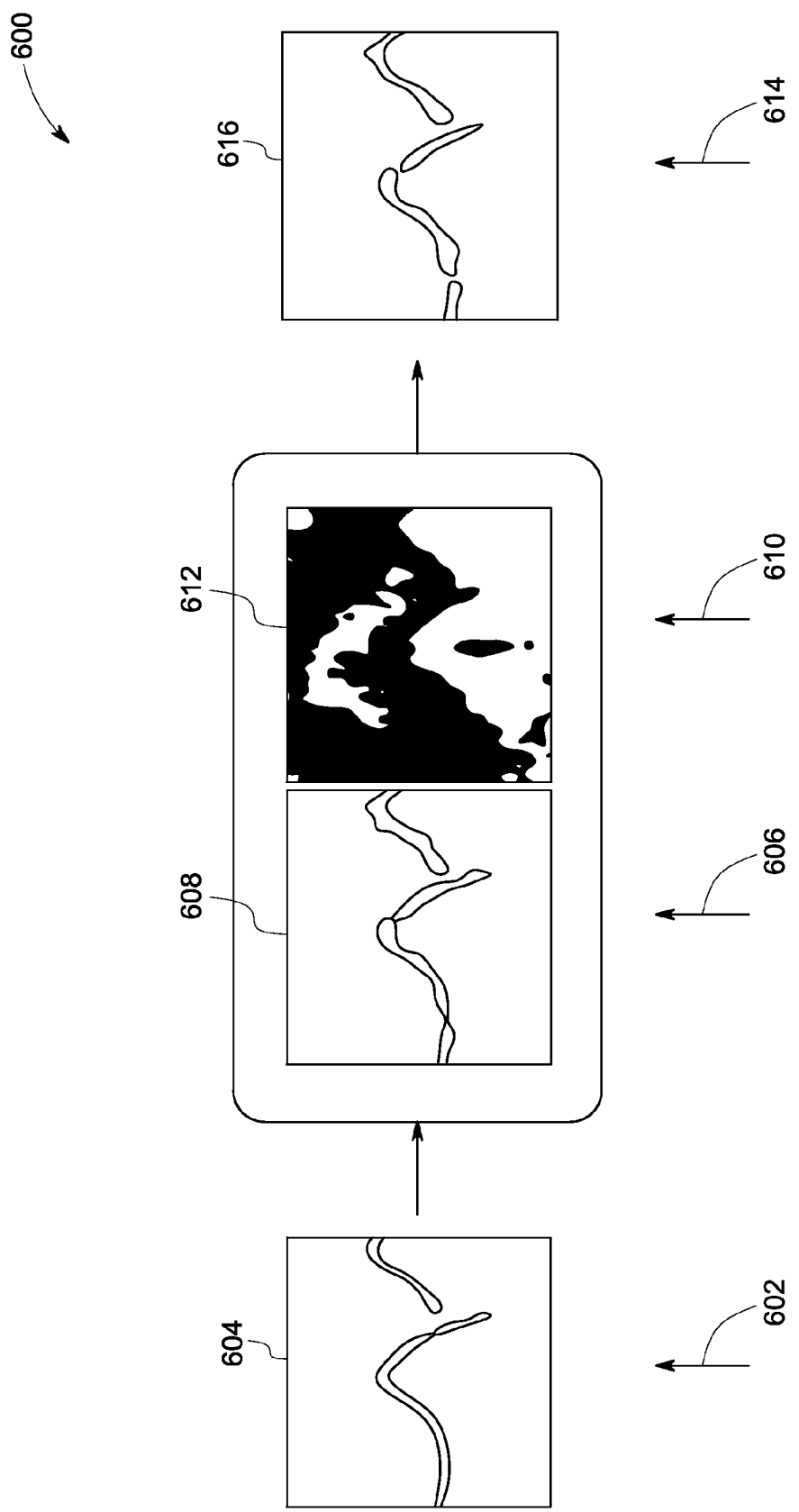
FIG. 6 is a diagrammatic illustration of a step of identifying a bone surface in the method of FIG. 4, in accordance with aspects of the present technique.

Referring now to FIG. 6, a diagrammatical illustration 600 of the bone surface extraction of step 406 of FIG. 4 is depicted. By way of example, the method of FIG. 6 depicts the identification and extraction of the surface of the bone 502 (see FIG. 5). It may be noted that the method of FIG. 6 is described with reference to FIGS. 1-5. The method starts at step 602, where an ultrasound image 604 corresponding to the anatomical region of interest, such as the bone joint 500 (see FIG. 5) in the patient 102 (see FIG. 1) is obtained. The image 604 may be representative of a normal bone joint, for example.

Furthermore, at step 606, a reflection image 608 of the bone joint of interest is obtained. By way of example, the ultrasound probe 104 (see FIG. 1) is used to direct acoustic waves towards the bone joint and the reflected image 608 is generated using the reflected acoustic waves. As previously noted, the characteristic ultrasound image representation of the bone surface that is based on the acoustic "shadow" under the bone surface is employed to facilitate an automated identification of the bone surface. Accordingly, a specific image processing filter, such as a shadow mask 612 that is tailored to generate a strong response at the surface of the bone is generated, as depicted by step 610. Subsequently, at step 614, the shadow mask 612 is employed to enable the automated identification of bone surface from the ultrasound image 608. Particularly, the ultrasound image 608 is processed via use of the shadow mask 612 to generate an image 616 that depicts the "bone-likelihood." Once the bone-likelihood is identified, the bone surface is identified and extracted. Consequent to the processing of step 614, the bone surface is identified and extracted.

Figure 7:
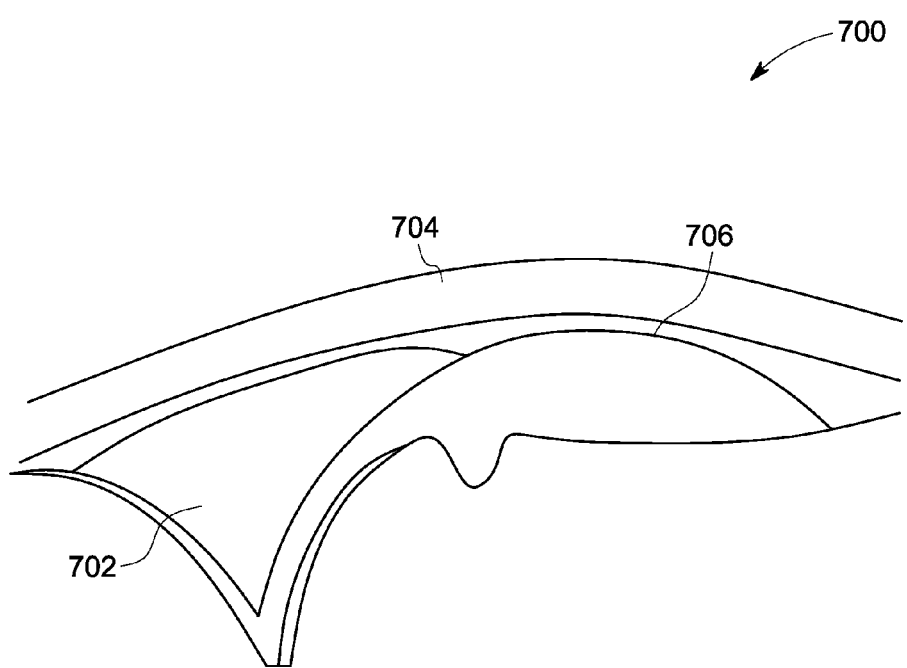
FIG. 7 is a diagrammatical illustration of a meta-carpophalangeal joint.

As previously noted, once the bone surface 408 (see FIG. 4) is identified and extracted, the joint capsule region is segmented based on the identified bone surface. FIG. 7 is a diagrammatical representation 700 of a meta-carpophalangeal (MCP) joint. Reference numeral 702 is representative of the joint capsule region. Also, an extensor tendon is represented by reference numeral 704, while a dorsal metacarpal synovial recess is represented by reference numeral 706. In accordance with aspects of the present technique, it is desirable to segment the joint capsule region 702. Particularly, the joint capsule region 702 is extracted based on the identified bone surface 408 of FIG. 4.

Figure 8:
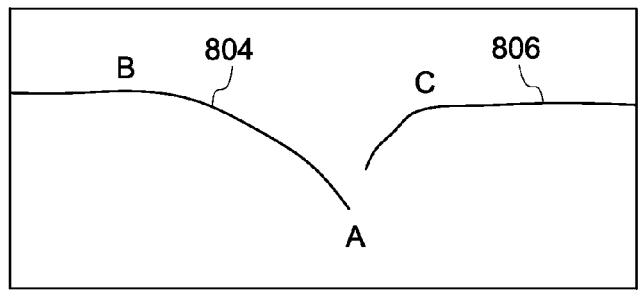
FIG. 8 is a diagrammatic illustration of a step of segmenting a joint capsule region using the bone surface in the method of FIG. 4, in accordance with aspects of the present technique.
Figure 8:
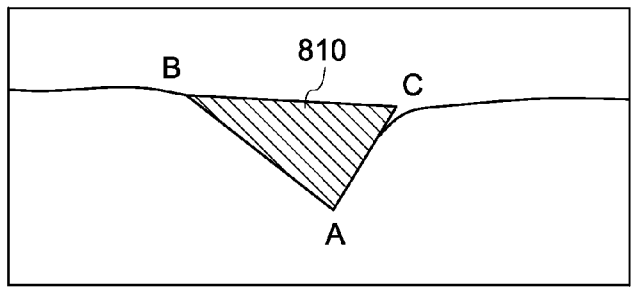
Figure 8:
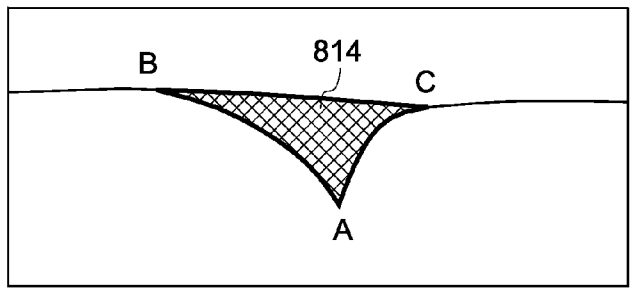
Figure 8:
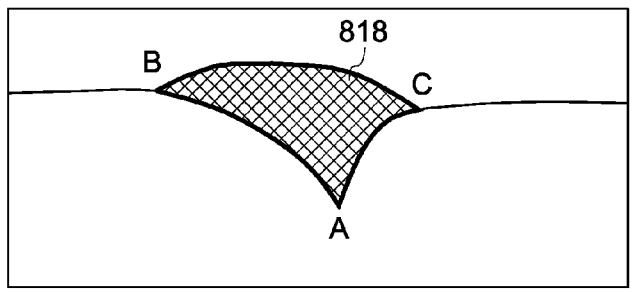

Turning now to FIG. 8, a diagrammatical representation 800 of the joint capsule region segmentation of step 410 of FIG. 4 is depicted. By way of example, the method of FIG. 8 depicts the identification and segmentation of the joint capsule region 702 (see FIG. 7). It may be noted that the method of FIG. 8 is described with reference to FIGS. 1-7. As previously noted, in accordance with aspects of the present technique, a joint capsule region, such as the joint capsule region 702 (see FIG. 7) is segmented based on the identified bone surface. Specifically, FIG. 8 depicts an automated segmentation of the joint capsule region using the extracted bone surface to provide contextual hints or indications about the location of the joint capsule region. In one embodiment, an anatomical model of the joint using certain measurements corresponding to the joint may be used to aid in the segmentation of the joint capsule region.

However, in certain other embodiments, the joint capsule region is segmented using expert annotation of the anatomy on a few control (normal) datasets in order to generate normalized representative shapes and statistical priors for the joint capsule region given the bone surface. Accordingly, one example of a model/atlas based segmentation of the joint capsule region, in accordance with aspects of the present technique, is presented in FIG. 8.

The method starts at step 802, where a bone surface that has been identified and extracted is considered. In the example of FIG. 8, the bone surface is depicted as including a first bone surface 804 and a second bone surface 806 that form the joint. Furthermore, at step 802, given the identified bone surfaces 804, 806, a point 'A' on the bone that is farthest from the probe 104 (see FIG. 1) is identified. Additionally, points 'B' and 'C' where the two bone surfaces 804 and 806 start curving towards point 'A' are identified.

Subsequently, at step 808, these three points 'A', 'B', 'C' are connected to form a triangle 810. This triangle 810 is used to provide an initial or first guess of the location of the joint capsule region. Moreover, at step 812, regions of the triangle 810 that are above the bone surfaces 804, 806 are retained. By way of example, regions of the triangle 810 that lie above the bone surfaces 804 and 806, but below line BC are retained. These regions are representative of an approximation of the model/atlas based prior for the joint capsule region since the known anatomical structure of the joint is employed. Also, a prior-likelihood 814 of the joint capsule region based on the already identified bone surfaces 804, 806 is generated.

Additionally, using this prior-likelihood 814, the joint capsule region is segmented, as indicated by step 816. A variety of segmentation techniques may be used to segment the joint capsule region. By way of example, a region growing technique may be employed to segment the joint capsule region. It may be noted that region growing is a simple region-based image segmentation method. The region growing technique typically entails selection of initial seed points. Subsequently, neighboring pixels of the initial "seed points" are examined to determine whether the pixel neighbors should be added to the region. This process may be iteratively performed until a consensus is reached. Reference numeral 818 is representative of the segmented joint capsule region.

In accordance with aspects of the present technique, the segmented joint capsule region 818 (see FIG. 8) is employed as a region of interest to perform measurements that allow determination whether the joint is diseased or not. Accordingly, the extracted bone surfaces 804, 806 (see FIG. 8) and/or the segmented joint capsule region 818 are analyzed to identify presence of a disease state in the joint capsule region. Additionally, a quantification of the identified disease state is also generated, in accordance with aspects of the present technique.

As previously noted, the analysis module 308 (see FIG. 3) is employed in the identification and/or quantification of the disease state. In one embodiment, joint capsule volume, blood-flow inside the joint capsule region, echogenicity of the joint capsule region, are some examples of measurements that can be made within the segmented joint capsule region. These measurements are then compared with similar measurements made on known normal (control) joint images. As previously noted, the measurements corresponding to the known normal joint images may be obtained from the normal model database 314 (see FIG. 3). This comparison facilitates an automated differentiation between the normal and abnormal joints. According to further aspects of the present technique, apart from differentiating between the diseased and normal joints, such measurements are also used to provide a qualitative and/or quantitative score about the "health" of the joint. Additionally, these measurements are used to determine the efficacy of therapy on the disease state and/or to track the progression of the disease state in the joint.

Furthermore, in certain embodiments, the measurements are obtained using expert annotation on numerous control (normal) subjects to understand the statistics of normal measurements. In addition, the measurements are normalized by the size of the anatomy in order to be applicable to anatomy of any size. Moreover, these measurements are employed to aid in modeling the normal conditions. This normal model is used to identify the disease state. For example, the disease state is determined based on hypothesis testing comparisons of the determined measurements with the normal model.

In accordance with further aspects of the present technique, the state of the disease progression may be quantified. To that end, a distance metric between the normal statistics and the statistics measured from the test subject, such as the patient 102 is defined. For example, if the normal model is approximated by a Gaussian distribution around the mean values obtained from the normal measurements, then a suitable distance metric may be the Mahalanobis distance.

Moreover, in accordance with aspects of the present technique, apart from joint capsule based measurements, other pathologies, such as bone erosions may be identified and/or quantified. To that end, the identified bone surfaces are analyzed to identify candidate regions of bone erosions. Bone erosion can be geometrically characterized as a sudden change in the smoothness of the bone surface. Accordingly, a change in the curvature (K) of the bone surface is computed at any point on the bone surface. In one embodiment, the change in the curvature of the bone surface is determined by computing the rate of change of the unit-normal to the bone surface at that point. Alternatively, other geometric properties such as area invariants may also be used to detect abnormalities on the bone surface that mimic the geometric properties of bone erosion.

Figure 9:
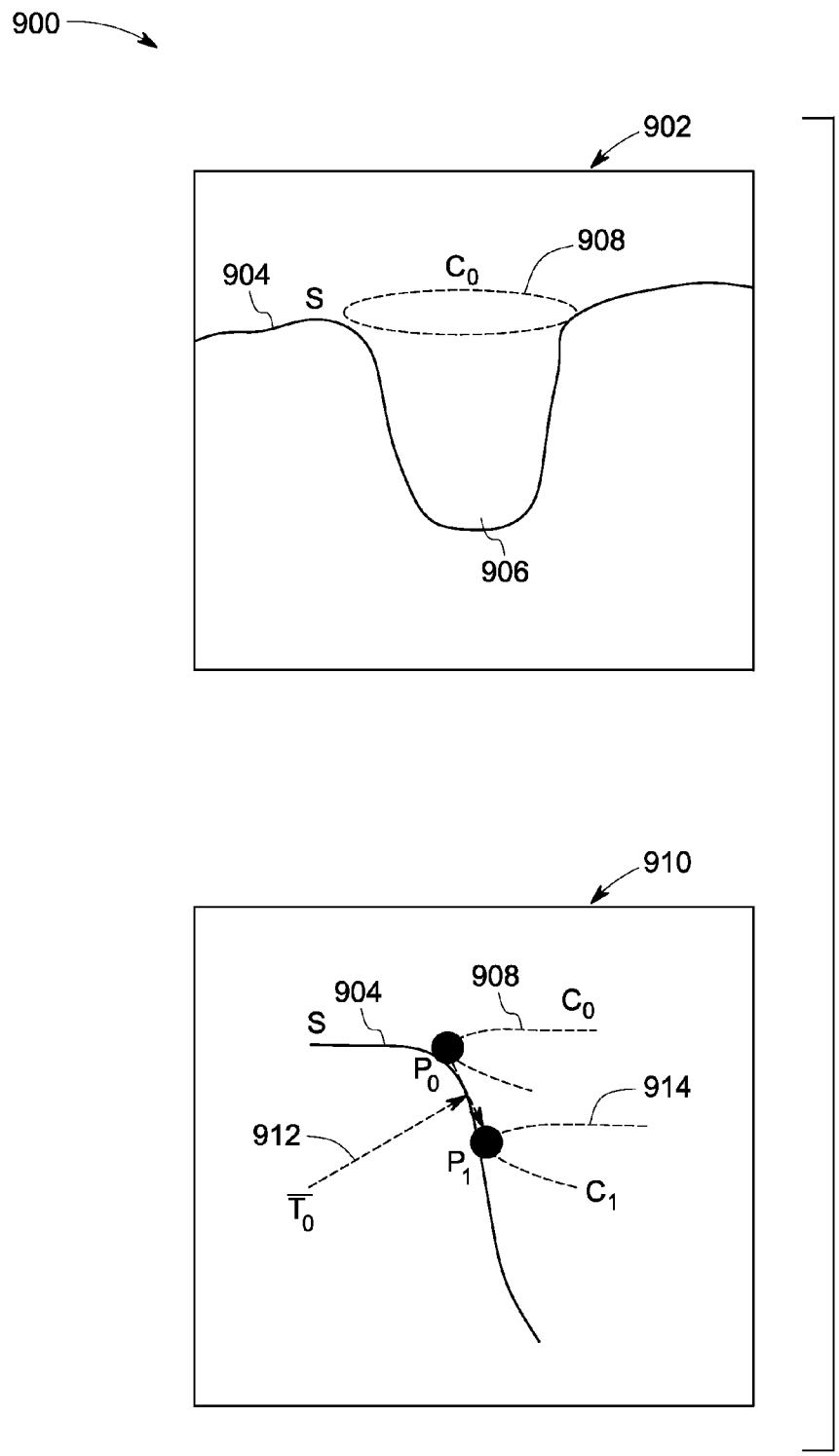
FIG. 9 is a diagrammatic illustration of a step of determining a volume of a bone erosion in the method of FIG. 4, in accordance with aspects of the present technique.

Once the candidate site of bone erosion is identified, volumetric measures of the size of the bone erosion are automatically generated. In one embodiment, the volume of the bone erosion may be determined by an automated 3D hole-filling followed by measuring the amount of bone filled in. Alternative methods of determining volumetric measures of the bone erosion are also contemplated. Accordingly, an exemplary method for determining the volumetric measures of the bone erosion is presented. FIG. 9 is a diagrammatical illustration 900 of an exemplary method for determining the volumetric measures of the bone erosion. In particular, FIG. 9(a) is a diagrammatical illustration 902 of a step of fitting a contour to a bone surface along the bone erosion. Also, FIG. 9(b) is a diagrammatical illustration 910 of a step of evolving points along the surface of the bone erosion.

In one embodiment, the curvature or other geometric properties of a bone surface S 904 is employed to determine the volume of a bone erosion 906. For example, the curvature based processing of the identified bone surface S 904 allows fitting of a contour $C_0$ 908 through high curvature points around the edges of the bone erosion 906 as depicted in FIG. 9(a). Furthermore, it may be assumed that the bone surface S 904 is a 2D contour and is obtained by slicing the bone surface S 904 with a 3D plane such that the plane passes through the centroid of the contour $C_0$ 908. Subsequently, points on this contour $C_0$ 908 such a point $p_0$ are evolved along the direction of a tangent $\overline{T_0}$ 912 to the bone surface S 904 at the point $p_0$, as depicted in FIG. 9(b). This evolution is continued until the contour converges to a single point, for example.

In addition, this evolution process may be repeated to determine volumes corresponding to all contours. Reference numeral 914 is representative of a contour $C_1$ and $p_1$ is representative of a point on the contour $C_1$. Furthermore, in one example, the volume V of the bone erosion 906 is computed as a summation of the volumes of all the contours and is represented as:

$$V=\Sigma_{i=1}^{n}A(C_n)|\overline{T_n}|, \qquad (1)$$

where $A(C_n)$ is the area of the $n^{th}$ contour.

Also, once the location of the bone erosion 906 is determined, the location information may be communicated to the ultrasound probe 104 in order to re-scan that part of the anatomy at a higher resolution and to provide a region of interest for further color flow measurements in order to detect blood-flow inside or in the vicinity of the bone erosion 906.

Furthermore, the foregoing examples, demonstrations, and process steps such as those that may be performed by the system may be implemented by suitable code on a processor-based system, such as a general-purpose or special-purpose computer. It should also be noted that different implementations of the present technique may perform some or all of the steps described herein in different orders or substantially concurrently, that is, in parallel. Furthermore, the functions may be implemented in a variety of programming languages, including but not limited to C++ or Java. Such code may be stored or adapted for storage on one or more tangible, machine readable media, such as on data repository chips, local or remote hard disks, optical disks (that is, CDs or DVDs), memory or other media, which may be accessed by a processor-based system to execute the stored code. Note that the tangible media may comprise paper or another suitable medium upon which the instructions are printed. For instance, the instructions may be electronically captured via optical scanning of the paper or other medium, then compiled, interpreted or otherwise processed in a suitable manner if necessary, and then stored in the data repository 114 or memory.

The various embodiments of the exemplary methods and systems for the automated detection, quantification and/or tracking of pathologies using ultrasound images described hereinabove dramatically enhance early diagnosis, improve serial tracking, and reduce operator dependence in the assessment of rheumatoid arthritis at the point of care. Moreover, since the methods and detection, quantification and/or systems for automated tracking of pathologies are specialized for rheumatological use, treatment delays may be avoided and healthcare costs may be reduced. Additionally, an objective assessment of rheumatoid arthritis is provided by designing direct, joint-level measures of disease activity for pathologies related to rheumatoid arthritis. Use of these objective scoring methods lead to better-informed diagnosis, improved treatment planning and reduced time and cost of treatment for rheumatoid arthritis. Also, reduced operator dependence in the assessment of rheumatoid arthritis allows consistent serial tracking of disease progression by facilitating automated extraction of clinically relevant quantitative and qualitative information from the ultrasound images.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. An automated method for detecting a disease state, the method comprising:
   identifying a bone surface in each of one or more image data sets using a bone surface identifying module, wherein the one or more image data sets correspond to a region of interest in an object of interest, and wherein identifying the bone surface in each of the one or more image data sets comprises:
      obtaining a first image corresponding to the region of interest in a normal subject;
      obtaining a second image corresponding to the region of interest in the object of interest;
      identifying an acoustic shadow in the second image;
      generating a mask based on the identified acoustic shadow;
   segmenting a joint capsule region corresponding to each of the one or more image data sets based on a corresponding identified bone surface using a joint capsule segmenting module, wherein segmenting the joint capsule region comprises:
      developing an atlas of the region of interest;
      determining a point in the atlas that is disposed at a location farthest away from a determined position;
      identifying one or more points in the atlas where one or more bone surfaces forming the region of interest start curving towards the farthest point;
      ascertaining an initial estimate of a location of the joint capsule region;
      generating a prior likelihood for the joint capsule region based on the identified bone surface;
      segmenting the joint capsule region based on the prior likelihood; and
   analyzing the segmented joint capsule region to identify the disease state using an analysis module.

2. The method of claim 1, further comprising obtaining the one or more image data sets corresponding to the region of interest in the object of interest.

3. The method of claim 2, wherein the region of interest in the object of interest is a bone joint.

4. The method of claim 2, wherein obtaining the one or more image data sets comprises acquiring the one or more image data sets corresponding to the region of interest in the object of interest at different points in time.

5. The method of claim 1, further comprising processing the second image with the mask to identify a bone-likelihood.

6. The method of claim 5, further comprising extracting the bone surface based on the bone-likelihood.

7. The method of claim 1, wherein analyzing the segmented joint capsule region comprises:
   determining parameters corresponding to the segmented joint capsule region; and
   comparing the parameters corresponding to the segmented joint capsule region with parameters corresponding to the normal subject to identify the disease state.

8. The method of claim 7, wherein analyzing the segmented joint capsule region further comprises computing a metric indicative of a status of the identified disease state.

9. The method of claim 8, wherein analyzing the segmented joint capsule region further comprises determining a volume of a bone erosion in the region of interest.

10. The method of claim 9, wherein determining the volume of the bone erosion comprises:
    identifying one or more candidate regions of bone erosion by measuring a change in curvature of the bone surface;
    fitting one or more contours through edges of the region of bone erosion; and
    evolving one or more points on the one or more contours along a tangent to the bone surface to determine the volume of the one or more contours.

11. The method of claim 10, further comprising summing the volumes corresponding to the one or more contours to estimate the volume of the bone erosion.

12. The method of claim 11, further comprising registering the one or more image data sets based on the corresponding identified bone surfaces to generate a registered image.

13. The method of claim 12, further comprising visualizing the registered image, the extracted bone surface, the segmented joint capsule region, the identified disease state, or combinations thereof on a display.

14. An automated system for detecting a disease state, the system comprising:
    a detection platform, comprising:
       a bone surface identifying module configured to identify a bone surface in one or more image data sets, wherein the one or more image data sets correspond to a region of interest in an object of interest, and wherein for each of the one or more image data sets the bone surface identifying module is configured to:
          obtain a first image corresponding to the region of interest in a normal subject;
          obtain a second image corresponding to the region of interest in the object of interest;
          identify an acoustic shadow in the second image;
          generate a mask based on the identified acoustic shadow;
       a joint capsule segmenting module configured to determine a joint capsule region in the one or more image data sets based on a corresponding identified bone surface, wherein the joint capsule segmenting module is configured to:
          develop an atlas of the region of interest;
          determine a point in the atlas that is disposed at a location farthest away from a determined position;
          identify one or more points in the atlas where one or more bone surfaces forming the region of interest start curving towards the farthest point;

ascertain an initial estimate of a location of the joint capsule region;
generate a prior likelihood for the joint capsule region based on the identified bone surface;
segment the joint capsule region based on the prior likelihood; and
an analysis module configured to identify the disease state in the segmented joint capsule region.

15. The system of claim 14, further comprising a registration module configured to register the one or more image data sets based on the identified bone surfaces corresponding to the one or more image data sets to generate a registered image.

16. A non-transitory computer-readable non transitory media storing computer executable code to perform the method of:
identifying a bone surface in each of one or more image data sets, wherein the one or more image data sets correspond to a region of interest in an object of interest, and wherein identifying the bone surface in each of the one or more image data sets comprises:
obtaining a first image corresponding to the region of interest in a normal subject;
obtaining a second image corresponding to the region of interest in the object of interest;
identifying an acoustic shadow in the second image;
generating a mask based on the identified acoustic shadow;
segmenting a joint capsule region corresponding to the one or more image data sets based on a corresponding identified bone surface, wherein segmenting the joint capsule region comprises:
developing an atlas of the region of interest;
determining a point in the atlas that is disposed at a location farthest away from a determined position;
identifying one or more points in the atlas where one or more bone surfaces forming the region of interest start curving towards the farthest point;
ascertaining an initial estimate of a location of the joint capsule region;
generating a prior likelihood for the joint capsule region based on the identified bone surface;
segmenting the joint capsule region based on the prior likelihood; and
analyzing the segmented joint capsule region to identify the disease state.

17. The non-transitory computer-readable media of claim 16, storing computer executable code to perform the method of:
registering the one or more image data sets using the identified bone surfaces corresponding to the one or more data sets to generate a registered image.

18. An imaging system, the system comprising:
an acquisition subsystem configured to obtain a plurality of image data sets corresponding to a region of interest in an object of interest;
a processing subsystem in operative association with the acquisition subsystem and comprising a detection platform, wherein the detection platform comprises:
a bone surface identifying module configured to identify a bone surface in one or more image data sets, wherein the one or more image data sets correspond to a region of interest in an object of interest, and wherein for each of the one or more image data sets the bone surface identifying module is configured to:
obtain a first image corresponding to the region of interest in a normal subject;
obtain a second image corresponding to the region of interest in the object of interest;
identify an acoustic shadow in the second image;
generate a mask based on the identified acoustic shadow;
a joint capsule segmenting module configured to determine a joint capsule region in the one or more image data sets based on a corresponding identified bone surface, wherein the joint capsule segmenting module is configured to:
develop an atlas of the region of interest;
determine a point in the atlas that is disposed at a location farthest away from a determined position;
identify one or more points in the atlas where one or more bone surfaces forming the region of interest start curving towards the farthest point;
ascertain an initial estimate of a location of the joint capsule region;
generate a prior likelihood for the joint capsule region based on the identified bone surface;
segment the joint capsule region based on the prior likelihood; and
an analysis module configured to identify a disease state in the segmented joint capsule region.

19. The system of claim 18, further comprising a registration module configured to register one or more image data sets based on the identified bone surfaces corresponding to the one or more image data sets to generate a registered image.

* * * * *